United States Patent
Park et al.

(10) Patent No.: US 11,497,821 B2
(45) Date of Patent: Nov. 15, 2022

(54) METHOD FOR LABELING RADIOISOTOPE, RADIOLABELING COMPOUNDS USING QUINONE COMPOUND AND KIT COMPRISING THE SAME FOR LABELING RADIOISOTOPE

(71) Applicant: KOREA ATOMIC ENERGY RESEARCH INSTITUTE, Daejeon (KR)

(72) Inventors: Sang Hyun Park, Seoul (KR); Sajid Mushtaq, Jeongeup-si (KR); Dae Seong Choi, Jeollabuk-do (KR)

(73) Assignee: Korea Atomic Energy Research Institute, Daejeon (KR)

( * ) Notice: Subject to any disclaimer, the term of this patent is extended or adjusted under 35 U.S.C. 154(b) by 41 days.

(21) Appl. No.: 16/897,894

(22) Filed: Jun. 10, 2020

(65) Prior Publication Data

US 2020/0390914 A1    Dec. 17, 2020

(30) Foreign Application Priority Data

Jun. 12, 2019 (KR) ........................ 10-2019-0069419

(51) Int. Cl.
| | |
|---|---|
| *A61K 51/08* | (2006.01) |
| *A61K 47/54* | (2017.01) |
| *C07C 13/45* | (2006.01) |

(52) U.S. Cl.
CPC .......... *A61K 51/088* (2013.01); *A61K 47/555* (2017.08); *C07C 13/45* (2013.01); *A61K 2123/00* (2013.01); *C07C 2602/24* (2017.05)

(58) Field of Classification Search
CPC ........ A61K 51/00; A61K 51/04; A61K 51/08; A61K 51/081; A61K 51/082; A61K 51/088; A61K 51/1244; A61K 2121/00; A61K 2123/00; A61K 47/00; A61K 47/555; A61P 35/00; C07C 13/45; C07C 2602/24; C07B 59/008; C07B 59/001; C07B 2200/05; C07K 1/13; C07K 5/0817; C07K 14/79; C07K 14/765; G01N 33/60
USPC .......... 424/1.11, 1.49, 1.53, 1.65, 1.69, 2.81, 424/1.85, 1.89, 9.1, 9.2, 9.3, 9.4, 9.5, 9.6
See application file for complete search history.

(56) References Cited

FOREIGN PATENT DOCUMENTS

| | | |
|---|---|---|
| EP | 2974744 A1 | 1/2016 |
| WO | 2006/050262 A2 | 5/2006 |

OTHER PUBLICATIONS

Borrmann et al, Bioconjugate Chemistry, vol. 26, pp. 257-261 (Year: 2015).*
Zoltan Banoczi, et al., "Amino acid and peptide bioconjugates", Amino Acids, Peptides and Proteins, Vo. 42, 2018, pp. 103.

* cited by examiner

*Primary Examiner* — D. L. Jones
(74) *Attorney, Agent, or Firm* — Fox Rothschild LLP

(57) ABSTRACT

The present disclosure relates to a method for labeling a biomolecule, a fluorescent dye, or a nanoparticle compound with a radioisotope, comprising: (a) providing a cyclooctyne compound represented by the following formula (I) comprising the biomolecule, the fluorescent dye, or the nanoparticle compound which is bound to a cyclooctyne moiety of the cyclooctyne compound; and (b) reacting the cyclooctyne compound of formula (I) with a quinone compound represented by the following formula (II) to give a biomolecule, a fluorescent dye, or a nanoparticle compound labeled with the radioisotope:

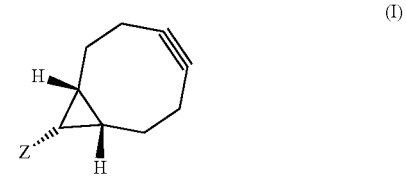

(I)

in formula (I), (Z is the biomolecule, the fluorescent dye, or the nanoparticle compound)

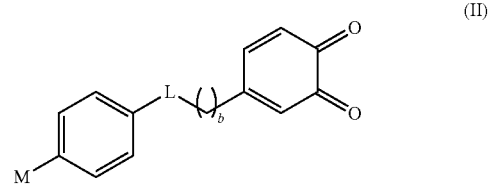

(II)

in formula (II), (b is 0 or an integer from 1 to 10; L is $CH_2$, —COO—, or —CONH—; M is the radioisotope).

9 Claims, 3 Drawing Sheets

METHOD FOR LABELING RADIOISOTOPE, RADIOLABELING COMPOUNDS USING QUINONE COMPOUND AND KIT COMPRISING THE SAME FOR LABELING RADIOISOTOPE

CROSS-REFERENCE TO RELATED APPLICATION(S)

This application claims benefit of priority to Korean Patent Application No. 10-2019-0069419 filed on Jun. 12, 2019 in the Korean Intellectual Property Office, the disclosure of which is incorporated herein by reference in its entirety.

BACKGROUND

1. Field

The present disclosure relates to a method for labeling a radioisotope using a quinone compound, a radiolabeling compound using a quinone compound, and a kit including the same, and more particularly, a technology using a method for labeling a radioisotope using a quinone compound, a radiolabeling compound using a quinone compound, and a kit including the same, having a relatively fast reaction rate without using an organic solvent, a radioisotope labeling kit including the same, which may be applied in the field of medical diagnosis and treatment.

2. Description of Related Art

In order to use physiologically active substances such as peptides, proteins, antibodies, or the like for a molecular imaging process, disease diagnosis and treatment processes, or the like, radiolabeling technologies of biomolecules have been developed. The prior art inventions have mainly used a method of conjugating a chelator to a physiologically active substance. This method chemically introduced a separate chelator into the physiologically active substance, but had fundamental limitations to improve relatively low reaction rates, or reaction conditions, not suitable for physiologically active substances, such as relatively high temperature, acidic or basic reactions, a reaction solvent having toxicity, or the like, when the chelator is conjugated.

For example, radioactive iodine has been used for decades for radiolabeling biomolecules for diagnostic and therapeutic purposes. Specifically, $^{124}$I was radioactive iodine mainly used for a positron emission tomography (PET) process, $^{123}$I and $^{125}$I were radioactive iodines mainly used for a single photon emission computed tomography (SPECT) process, and $^{131}$I has mainly been used for diagnosis and treatment of diseases such as a thyroid cancer.

As described above, as radioactive iodine is widely used in medicine, various methods for labeling radioactive iodine on biomolecules and relatively small molecules have been developed. Thereamong, an electrophilic aromatic substitution reaction has been shown to be a method capable of labeling directly a radioisotope, and to have relatively high efficiency. However, since most labeling compounds synthesized by the labeling method were unstable in animal bodies, desired image results has been not often obtained, and a relatively strong oxidant used for the labeling operation has been shown to deteriorate physiological activity of the biological material. In order to solve the above problems, a method of indirectly labeling and synthesizing radioactive iodine has been studied to develop several prosthetic groups.

However, the method of indirectly labeling and synthesizing radioactive iodine developed to date has often resulted in random labeling compounds due to lack of chemical selectivity for an active group of a compound, and has required excessive substrate for a relatively high yield due to a relatively slow reaction rate.

Accordingly, there is a need for development of new radioactive iodine labeling methods that are stable in living cells and animals. In the related art, WO2006-050262, discloses a reaction using a cyclooctyne compound and an azide compound. However, use of organic solvents such as toluene, DMSO, and the like is required for such a reaction, and therefore, the use is partially limited to living cells and animals.

Under the circumstances, it is expected that a radiolabeling compound, and a biomolecule, a fluorescent dye, or a nanoparticle compound may be used to label a radioisotope into the biomolecule and the like in a relatively fast reaction rate and a relatively high radiochemical yield, and, in addition, when a radiolabeling compound is provided without requirement for use of an organic solvent, the radiolabeling compound may be usefully employed for labeling of the radioisotope into the biomolecule and the like, and medical diagnosis.

SUMMARY

An aspect of the present disclosure is to provide a method for labeling a radioisotope, having a relatively high reaction rate without using an organic solvent.

Another aspect of the present disclosure is to provide a radiolabeling compound, having a relatively fast reaction rate without using an organic solvent.

Another aspect of the present disclosure is to provide a kit for labeling a radioisotope, having a relatively fast reaction rate without using an organic solvent.

Another aspect of the present disclosure is to provide a biomolecule, a fluorescent dye, or a nanoparticle compound labeled with a radioisotope.

Another aspect of the present disclosure is to provide a medical diagnostic composition comprising the same.

Another aspect of the present disclosure to provide a composition for treating cancer, comprising the same.

According to an aspect of the present disclosure, a method for labeling a radioisotope includes providing a cyclooctyne compound represented by the following formula (I), and to which a biomolecule, a fluorescent dye, or a nanoparticle compound is bound; and reacting the cyclooctyne compound with a quinone compound represented by the following formula (II) and labeled with the radioisotope:

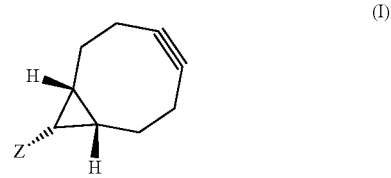

(I)

in formula (I), Z is the biomolecule, the fluorescent dye, or the nanoparticle compound,

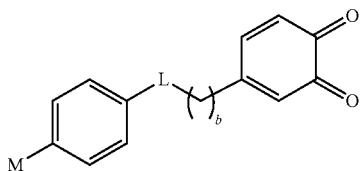

(II)

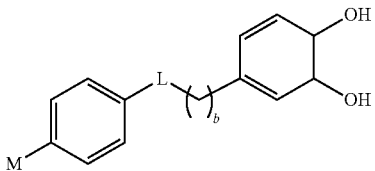

(IIa)

in formula (II), b is 0 or an integer from 1 to 10; L is CH$_2$, —COO—, or —CONH—; M is the radioisotope.

According to another aspect of the present disclosure, a radiolabeling compound represented by the following formula (II) or (IIa), for labeling a molecule having a cyclooctyne moiety is provided:

in formulas (II) and (IIa), b is 0 or an integer from 1 to 10; L is CH$_2$, —COO—, or —CONH—; M is the radioisotope.

According to another aspect of the present disclosure, a biomolecule, a fluorescent dye, or a nanoparticle compound represented by the following formula (III) and labeled with a radioisotope is provided:

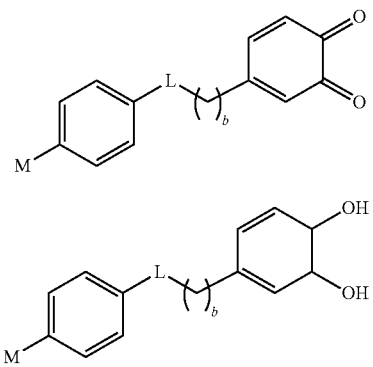

(II)

(IIa)

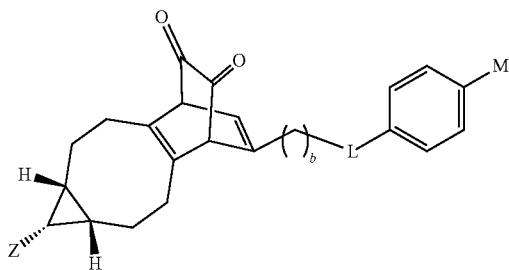

(III)

in formula (III), Z is a biomolecule, a fluorescent dye, or a nanoparticle compound; b is 0 or an integer from 1 to 10; L is CH$_2$, —COO—, or —CONH—; M is the radioisotope.

According to another aspect of the present disclosure, a composition for medical diagnosis, including the biomolecule, the fluorescent dye, or the nanoparticle compound represented by the above formula (III) and labeled with a radioisotope, as an active ingredient, is provided.

According to another aspect of the present disclosure, a composition for treating cancer, including the biomolecule, the fluorescent dye, or the nanoparticle compound represented by the above formula (III) and labeled with a radioisotope, as an active ingredient, is provided.

in formulas (II) and (IIa), b is 0 or an integer from 1 to 10; L is CH$_2$, —COO—, or —CONH—; M is the radioisotope.

According to another aspect of the present disclosure, a kit for labeling a radioisotope, includes a cyclooctyne compound represented by the following formula (I), and to which a biomolecule, a fluorescent dye, or a nanoparticle compound is bound; and a quinone compound represented by the following formula (II) or (IIa) and labeled with the radioisotope:

BRIEF DESCRIPTION OF DRAWINGS

The above and other aspects, features, and advantages of the present disclosure will be more clearly understood from the following detailed description, taken in conjunction with the accompanying drawings, in which.

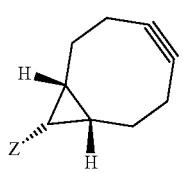

(I)

Figure 1:
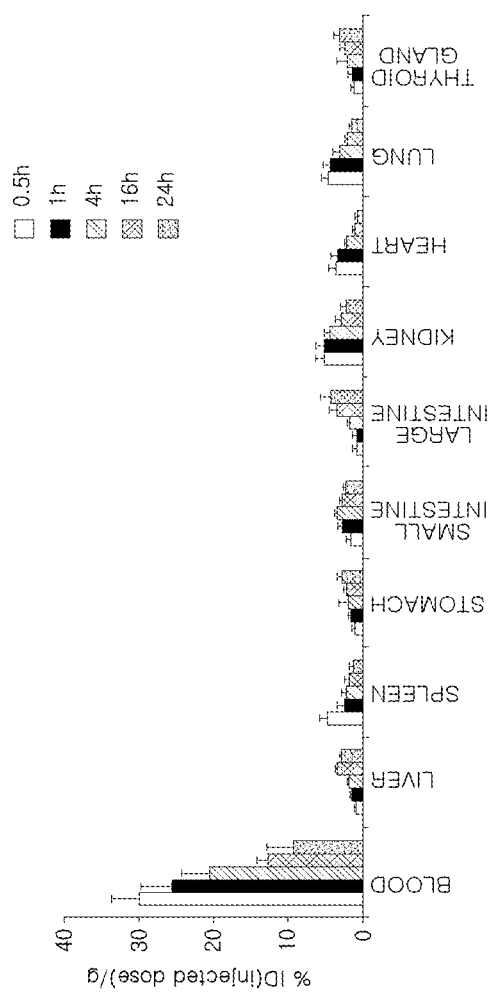
FIG. 1 shows biodistribution results of radioiodinated HSA [$^{125}$I] 7, n=5 male mice per group.

in formula (I), Z is the biomolecule, the fluorescent dye, or the nanoparticle compound,

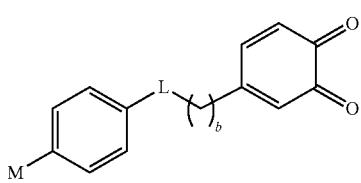

(II)

DETAILED DESCRIPTION

Hereinafter, with reference to the accompanying drawings will be described a preferred embodiment of the present disclosure. However, embodiments of the present disclosure may be modified in various other forms, but the scope of the present disclosure is not limited to the embodiments described below.

According to the present disclosure, a radiolabeling compound with markedly improved accumulation on the thyroid gland may be provided, and, more particularly, a quinone compound with a radioisotope may be provided, and the compound may also be referred to as a "tracer." The tracer of the present disclosure may label a radioisotope at a relatively high reaction rate and a relatively high radiochemical yield, by a cyclization reaction with a biomolecule, a fluorescent dye, or a nanoparticle compound containing a cyclooctyne moiety.

More specifically, according to the present disclosure, a method for labeling a radioisotope, including providing a cyclooctyne compound represented by the following formula (I), to which a biomolecule, a fluorescent dye, or a nanoparticle compound is bound; and reacting the cyclooctyne compound with a quinone compound represented by the following formula (II) and labeled with the radioisotope:

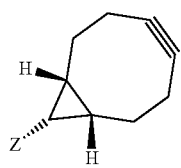

(I)

in formula (I), Z is the biomolecule, the fluorescent dye, or the nanoparticle compound,

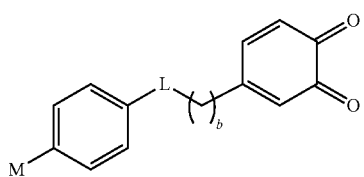

(II)

in formula (II), b is 0 or an integer from 1 to 10; L is $CH_2$, —COO—, or —CONH—; M is the radioisotope.

The reacting may be carried out at room temperature and atmospheric (ambient) conditions, and may have advantages that do not require relatively high temperature, acidic or basic reactions, a reaction solvent having toxicity, use of organic solvent, and the like.

In this case, the room temperature may be 10 to 40° C., for example 25 to 35° C. A pH atmosphere for obtaining the compound is not particularly limited to pH 1 to 14, but preferably pH ranges, close to neutral, for example, pH 6 to 8.

The solvent used in a reaction of the present disclosure is not particularly limited, but may be preferably water, for example, an aqueous solution or the like. Use of an organic solvent such as DMSO is not required. Therefore, the reacting may be, for example, performed in an aqueous phase, for example, an aqueous solution.

The biomolecule may be at least one selected from the group consisting of a peptide, an affibody, an antibody, and an oligonucleotide; the nanoparticle compound may be at least one selected from the group consisting of a metal nanoparticle, a synthetic polymer nanoparticle, and a biopolymer nanoparticle; and the metal nanoparticle may be any one metal selected from the group consisting of gold (Au), platinum (Pt), palladium (Pd), silver (Ag), and copper (Cu), or an oxide of any one metal selected from the group consisting of cobalt (Co), manganese (Mn), iron (Fe), nickel (Ni), gadolinium (Gd), molybdenum (Mo), zinc (Zn), and chromium (Cr). The fluorescent dye may be at least one selected from a cyanine dye, a fluorescein dye, and a rhodamine dye.

In this case, the peptide may be a cancer targeting peptide, and may include an RGD peptide, a CGNSNPKSC peptide, a VHSPNKK peptide, a CTTHWGFTLC peptide, an SGKGPRQITAL peptide, an SGRSA peptide, an FSRYLWS peptide, or the like, preferably, an RGD peptide.

In addition, the affibody is not particularly limited, but may include a small molecule of 7 KDa or less than 7 KDa, which may bind to proteins, such as an Aβ peptide, an Apolipo protein A1, a CD25, a CD28, a c-Jun, an EGFR, a Factor VIII, a Fibrinogen, a Gp120, an HER2, an IgA, an IgE, an IgM, an IL-8, an Insulin, an RSV G protein, a Taq polymerase, a TNF-α, a Transferrin, a Transthyretin, or the like.

Furthermore, the antibody is not limited, but may include an Anti-VEGFR, an Anti-ERBB2, an Anti-CD20, an Anti-CD19, an Anti-CD22, an Anti-CD33, an Anti-CD25, an Anti-HLA-DR 10β, an Anti-tenascin, an Anti-CEA, an Anti-MUC1, an Anti-TAG 72, or the like.

In addition, the oligonucleotide is not limited, but may include DNA, RNA, siRNA, an antisense oligonucleotide, or the like.

The metal nanoparticle is not limited, but may include a metal nanoparticle which consist of a metal such as gold (Au), platinum (Pt), palladium (Pd), silver (Ag), copper (Cu), or the like; or an oxide of a metal such as cobalt (Co), manganese (Mn), iron (Fe), nickel (Ni), gadolinium (Gd), molybdenum (Mo), zinc (Zn), chromium (Cr), or the like, preferably, may be a gold nanoparticle or an iron nanoparticle.

In addition, the synthetic polymer nanoparticle is not limited, but may include poly(ethylene glycol), poly(vinyl alcohol), poly(acrylic acid), poly(hydroxyester), poly(s-caprolactone), poly(ortho-ester), polanhydride, polyphosphagene, poly(propylenefumarate), poly(glycolic acid), poly (lactic acid), poly(lactic-co-glycolic acid), poly (hydroxybutyate), poly(hydroxybutyrate-co-valerate), poly (urethane), poly(methyl methacrylate), or the like.

Further, the biopolymer nanoparticle is not limited, but may include chitin, chitosan, polylysine, hyaluronic acid, alginic acid, dextran, cellulose, or the like.

In addition, the nanoparticle compound may have a size of 1 nm to 1000 nm, preferably 10 nm to 500 nm, and more preferably 50 nm to 200 nm. When a size of the nanoparticle compound is less than 1 nm, it may be difficult to manufacture a nanoparticle compound labeled with radioactive iodine, according to the present disclosure. When a size of the nanoparticle compound exceeds 1000 nm, intrinsic properties of the nanoparticle compound may be lost.

The fluorescent dye may be at least one selected from a cyanine dye, a fluorescein dye, and a rhodamine dye.

The radioisotope which may be applied to the present disclosure may be selected from the group consisting of I, F, Tc, Re, Ga, In, Zr, Y, Ho, Sm, and Lu, for example, may be a diagnostic radioisotope such as I-125, F-18, Sc-44, Ga-67, Ga-68, Zr-89, Tc-99m, In-111, or the like, or other therapeutic radioisotopes such as Sc-47, Y-90, Sm-153, Ho-166, Lu-177, Re-188, Pb-212, Bi-213, Th-232, or the like. The radioisotope which may be applied to the present disclosure is not limited thereto, but may include alpha-ray-emitting nuclides and beta-ray-emitting nuclides, which may be therapeutic radioisotopes used for treatment of cancer, and positron-emitting nuclides and gamma-emitting nuclides, which may be diagnostic radioisotopes for diagnosis, without any limitation thereto. Preferably, the radioisotope M may be I or F.

The radioactive iodine may be at least one radioactive iodine selected from the group consisting of, for example, $^{122}$I, $^{123}$I, $^{124}$I, $^{125}$I, $^{127}$I, $^{131}$I, and $^{132}$I, preferably $^{125}$I.

According to another aspect of the present disclosure, a radiolabeling compound represented by the following formula (II) or (IIa), for labeling a molecule having a cyclooctyne moiety may be provided:

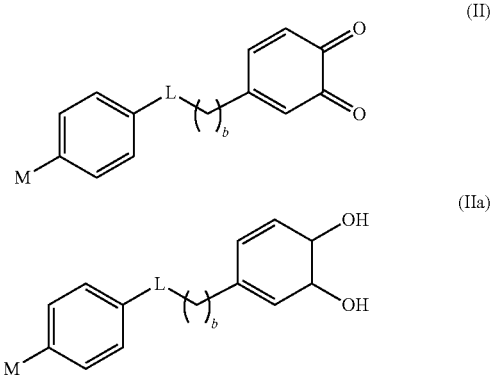

in formulas (II) and (IIa), b is 0 or an integer from 1 to 10; L is CH$_2$, —COO—, or —CONH—; M is the radioisotope.

In this case, in a case of using the radiolabeling compound represented by the formula (IIa), the compound of formula (II) may be obtained by further performing an operation of oxidizing an —OH group of a dihydroxyphenyl moiety to an =O group. In this case, the method of performing the oxidation operation is not particularly limited, and may be performed using, for example, sodium periodate (NaIO$_4$).

As described above, the quinone compound labeled with the radioisotope, used in the present disclosure, may be applied as a radiolabeling compound for labeling a molecular having a cyclooctyne moiety.

According to another aspect of the present disclosure, a kit for labeling a radioisotope, including a cyclooctyne compound represented by the following formula (I), and to which a biomolecule, a fluorescent dye, or a nanoparticle compound is bound; and a quinone compound represented by the following formula (II) or (IIa) and labeled with the radioisotope, may be provided. The kit of the present disclosure may be based on the method of the present disclosure described above, and all of the above-mentioned contents may be applied in the same manner:

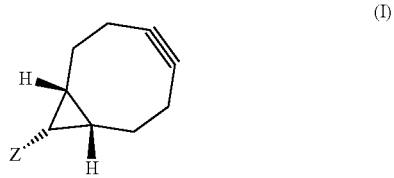

in formula (I), Z is the biomolecule, the fluorescent dye, or the nanoparticle compound,

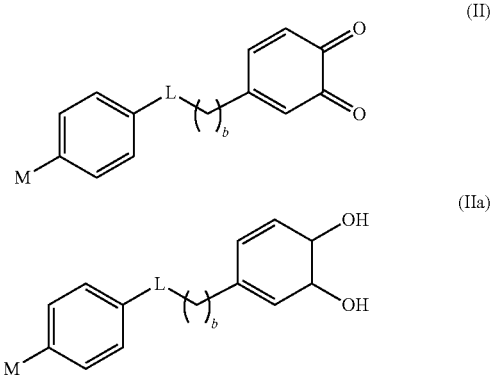

in formulas (II) and (IIa), b is 0 or an integer from 1 to 10; L is CH$_2$, —COO—, or —CONH—; M is the radioisotope.

In this case, in a case of using the radiolabeling compound represented by the formula (IIa), the compound of formula (II) may be obtained by further performing an operation of oxidizing an —OH group of a dihydroxyphenyl moiety to an =O group. In this case, the method of performing the oxidation operation is not particularly limited, and may be performed using, for example, sodium periodate (NaIO$_4$).

For example, the biomolecule may be at least one selected from the group consisting of a peptide, an affibody, an antibody, and an oligonucleotide; the nanoparticle compound may be at least one selected from the group consisting of a metal nanoparticle, a synthetic polymer nanoparticle, and a biopolymer nanoparticle; the metal nanoparticle may be any one metal selected from the group consisting of gold (Au), platinum (Pt), palladium (Pd), silver (Ag), and copper (Cu), or an oxide of any one metal selected from the group consisting of cobalt (Co), manganese (Mn), iron (Fe), nickel (Ni), gadolinium (Gd), molybdenum (Mo), zinc (Zn), and chromium (Cr); and the fluorescent dye may be at least one selected from a cyanine dye, a fluorescein dye, and a rhodamine dye.

According to another aspect of the present disclosure, a biomolecule, a fluorescent dye, or a nanoparticle compound represented by the following formula (III) and labeled with a radioisotope may be provided:

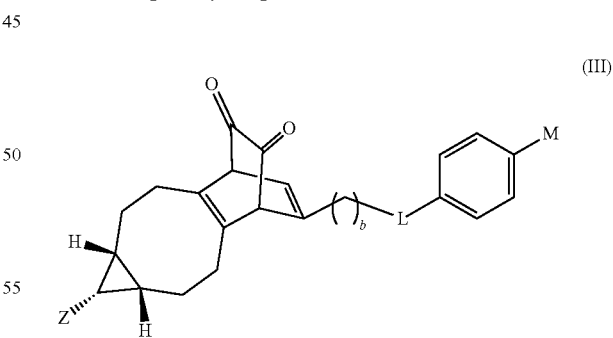

in formula (III), Z is a biomolecule, a fluorescent dye, or a nanoparticle compound; b is 0 or an integer from 1 to 10; L is CH$_2$, —COO—, or —CONH—; M is the radioisotope.

According to another aspect of the present disclosure, compositions for medical diagnosis and treatment, including the biomolecule, the fluorescent dye, or the nanoparticle compound represented by the above formula (III) and labeled with a radioisotope, as an active ingredient, may be provided.

The medical diagnosis is not particularly limited, but may include a single photon emission computed tomography (SPECT) process, a positron emission tomography (PET) process, a micro-PET process, a computed tomography (CT) process, a magnetic resonance imaging (MRI) process, or a diagnosis process by a target image of a radiation diagnostic device.

Furthermore, according to another aspect of the present disclosure, a composition for treating cancer, including the biomolecule, the fluorescent dye, or the nanoparticle compound represented by the above formula (III) and labeled with a radioisotope, as an active ingredient, may be provided.

The radioisotope may be $^{131}$I, and the cancer may be, for example, thyroid cancer.

The method for labeling radioactive iodine, according to the present disclosure, may use a compound represented by the formula (I) and/or (II) to label a biomolecule, a fluorescent dye, a nanoparticle compound, or a combination thereof with radioactive iodine at room temperature, without the use of additional organic solvents, and may be usefully used as the method for labeling radioactive iodine due to the relatively fast reaction rate and the relatively high radiochemical yield.

Therefore, according to the present disclosure, it may be expected that the resultants labeled with radioactive iodine may be effectively obtained for various target compounds, for example, peptides. In addition, the results may be expected to lead to development of radiopharmaceuticals that may be used in clinical as well as future studies.

Hereinafter, the present disclosure will be described in more detail with reference to specific examples. The following examples are merely examples to help understanding of the present disclosure, but the scope of the present disclosure is not limited thereto.

Example

1. Materials and Equipment

All chemicals, reagents, solvents, and materials including a human serum albumin protein (HSA) and a transferrin human protein (TF) were purchased from Sigma Aldrich and used without further purification. Peptide c[RGDyK] (FC-2202) was purchased from FUTURECHEM Co. Republic of Korea. All newly synthesized intermediate precursors were purified by silica gel chromatography, using high purity silica gel with average particle size 60 μm. The reaction progress was monitored using glass or aluminum based silica plates (60 F$_{254}$ pure silica gel). The compound spotted on TLC was visualized by using UV light wave length 254 nm or using staining agent and heating. The reactions were performed at low temperature (4° C.), or room temperature (25° C.). The NMR ($^1$H and $^{13}$C) analysis was performed using JEOL NMR spectrometer (500 MHz, KAERI, Jeongeup, Republic of Korea). The NMR spectra were obtained using chloroform-d (CDCl$_3$-d$_1$), dimethyl sulfoxide-d$_6$ (DMSO-d$_6$), or methanol-d$_4$ (CD$_3$OD) as solvent. The high resolution mass spectroscopy of low molecular weight precursors was performed at Korea Basic Science Institute (Seoul, Republic of Korea) using Bruker Q-TOF high resolution mass spectroscopy system. For the MALDI-TOF analysis of proteins and peptides, AB SCIEX TOF/TOF 5800 MALDI-TOF system (Korea Institute of Radiological & Medical Science, Seoul, Republic of Korea) was used. 3,5-dimethoxy-4-hydroxycinnamic acid (Sinapinic Acid) or 2,5-dihydroxybenzoic acid (DHB) was used as matrix for MALDI-TOF analysis. For biodistribution study accumulated radioactivity in each organ was measured using automatic gamma counter (PerkinElmer, USA). All SPECT/CT images were acquired using Inveon (Siemens) small-animal multimodality SPECT/CT system.

The cold and radioactive compounds were analyzed on analytical HPLC system supplied by Agilent Technologies. The analytical HPLC system (1290 infinite) was equipped with Eclipse XDB-C18 column (4.6×250 mm, 5 μm) and gamma detector. For HPLC purification Agilent Technologies preparative HPLC system (1260 infinite) equipped with gamma detector and Eclipse XDB-C18 column (7 μm, 21.2×150 mm) was used. All HPLC analysis were performed using solvent A (0.1% formic acid containing water) and solvent B (0.1% formic acid containing acetonitrile). For HPLC purification a preparative HPLC method A (flow rate: 10 mL/min, eluents gradient: 0-3 min: 95% A/5% B; 3-15 min: a linear gradient to 35% A/65% B from 95% A/5% B; 15-35 min: a linear gradient to 5% A/95% B from 35% A/65% B; 35-45 min: 5% A/95% B) or method B (flow rate: 10 mL/min, eluents gradient: 0-5 min: 95% A/5% B; 5-20 min: a linear gradient to 50% A/50% B from 95% A/5% B; 20-35 min: a linear gradient to 5% A/95% B from 50% A/50% B; 35-45 min: a linear gradient to 3% A/97% B from 5% A/95% B). The radioactive products were trapped in Sep Pak C18 cartridge preconditioned with 5 mL ethanol and 10 mL water. The aqueous solution of [$^{125}$I]NaI (in 0.1M NaOH) with a 25 mCi activity was purchased from PerkinElmer, Republic of Korea.

2. Synthesis of Quinone Compound (1) Synthesis of Intermediate Compound N-(3,4-dihydroxyphenethyl)-4-iodobenzamide (1)

4-iodobenzoic acid (1 g, 4 mmol) and HBTU coupling agent (1.5 g, 3.9 mmol) were dissolved in dimethylformamide DMF (10 mL). 4-(2-aminoethyl)benzene-1,2-diol hydrochloride (0.76 g, 4 mmol) and N,N-diisopropylethylamine (DIPEA) base (1 g, 7.7 mmol) were added under nitrogen gas atmosphere. The reaction mixture was stirred for 2.5 h and quenched by the addition of 1N HCl. The crude product was dissolved in ethyl-acetate and washed with saturated NaCl solution and dried using anhydrous Na$_2$SO$_4$. Crude product was purified by silica gel chromatography and ethyl-acetate/n-hexane (1:1) to give intermediate compound N-(3,4-dihydroxyphenethyl)-4-iodobenzamide (1) (0.9 g, 2.3 mmol, 58%). The HPLC retention time of product 1 was 22.0 min using method B.

$^1$H NMR (500 MHz, DMSO-d$_6$) δ8.722 (s, 1H), 8.609 (s, $^1$H), 8.550 (t, J=6.5 Hz, 1H), 7.797 (d, J=8.5 Hz, 2H), 7.556 (d, J=8.5 Hz, 2H), 6.406-6.596 (m, 3H, Ph), 3.319 (q, J=6.5 Hz, 2H), 2.593 (t, J=8.5, 2H); $^{13}$C NMR (125 MHz, DMSO-d$_6$) 165.862, 145.593, 144.058, 137.658, 133.825, 130.713, 129.655, 119.744, 116.511, 116.005, 99.161, 41.854, 35.073; HRMS ([M+H]$^+$) calculated: 384.1854; found: 384.1855.

(2) Synthesis of Intermediate Compound N-(3,4-dihydroxyphenethyl)-4-(tributylstannyl)benzamide (2)

The reagent bis(tributyltin) (1.5 g, 2.6 mmol), tetrakis(triphenylphosphine)palladium (Pd(PPh$_3$)$_4$) (0.15 g, 0.13 mmol), and intermediate compound 1 (0.5 g, 1.3 mmol) were dissolved in 25 mL of 1,4 dioxane. The reaction mixture was stirred under reflux for 16 h. The crude product was cooled to 25° C. and filtered through Whatman cellulose filter paper to remove undissolved impurities. The crude product was dissolved in ethyl-acetate and washed with saturated NaCl solution and dried using anhydrous $Na_2SO_4$. Crude product was purified by silica gel chromatography and ethyl-acetate/n-hexane (3:7) to give intermediate compound N-(3,4-dihydroxyphenethyl)-4-(tributylstannyl)benzamide (2) (0.9 g, 2.3 mmol, 700).

$^1$H NMR (500 MHz, DMSO-$d_6$) δ 8.732 (s, 1H), 8.616 (s, 1H), 8.442 (t, J=5.5 Hz, 1H), 7.695 (d, J=7.5 Hz, 2H), 7.470 (d, J=7.5 Hz, 2H), 6.415-6.602 (m, 3H, Ph), 3.343 (q, J=7.5 Hz, 2H), 2.597 (t, J=7.5 Hz, 2H), 1.401-1.559 (m, 6H), 1.211-1.284 (m, 6H), 0.956-1.136 (m, 6H), 0.806 (t, J=8.5 Hz, 9H); $^{13}$C NMR (125 MHz, DMSO-$d_6$) 166.845, 146.089, 145.593, 144.038, 136.551, 134.910, 130.799, 126.869, 119.744, 116.511, 116.005, 41.807, 35.206, 29.111, 27.204, 14.088, 9.720; HRMS ([M+H]$^+$) calculated: 548.3390; found: 548.3395.

3. Synthesis of Cyclooctyne Installed Compound

(1) Synthesis of BCN Installed cRGD Peptide 5a

Peptide (cRGDyK) (20 mg, 0.032 mmol) was added to the solution (1R,8S,9s)-Bicyclo[6.1.0]non-4-yn-9-ylmethylN-succinimidyl carbonate (BCN-succinimidyl ester) (9.3 mg, 0.31 mmol) of in DMSO (100 μL). The pH of solution was adjusted to 8.2-8.5 by using (DIPEA) (17 μL). The reaction was carried out for 2.5 h and the crude mixture was purified by preparative HPLC (method A) to give 5a (19 mg, 0.23 mmol, 74%, retention time: 15.9 min). MALDI-TOF ([M+H]$^+$) found: 796.4450.

(2) Synthesis of BCN Installed Transferrin Human 6a

Transferrin human protein (TF) (500 μM, pH 8.2, 100 μL, 1×PBS) was incubated with BCN-succinimidyl ester (20 mM, 10 μL in DMSO) for 4 h at 4° C. For the purification of 6a, crude product was diluted with saline (2.5 mL) and passed through a PD-10 desalting column. The extracted product was further subjected to centrifugation (4500 rpm, 12 min, 4° C.) using Amicon filter (30 kDa). BCN modified protein 6a was found in residue and analyzed using MALDI-TOF mass spectroscopy system and concentration (mg/mL) was determine using protein quantification system.

(3) Synthesis of BCN Installed Human Serum Albumin 7a

BCN installed human serum albumin protein was synthesized using same protocol as adopted for transferrin human protein.

4. Synthesis of Biomolecule Labeled with Radioisotope

Example 1: Radiosynthesis of $^{125}$I-cRGD Peptide ([$^{125}$I] 5)

(1) Synthesis of Compound [$^{125}$I]1

The synthesis of [$^{125}$I]1 was performed after slight modifications, according to a procedure published in "Radiosynthesis of $^{123}$I-labeled hesperetin for biodistribution study of orally administered hesperetin (Journal of Radioanalytical and Nuclear Chemistry, 306(2), pp. 437-443, 1. Jeon, J.".

Briefly, an intermediate precursor 2 (1 mg), obtained from 2. above, was dissolved in 1 mL of DMSO. 0.5 M of phosphoric acid (250 μL) and 0.5 M of peracetic acid (500 μL) were added. To start the reaction [$^{125}$I]NaI (2 mCi, 7 μL) in 0.1M NaOH was added and the reaction was carried out at room temperature for 10 min. The reaction was quenched by adding an excessive amount of aqueous sodium metabisulfite solution (0.5M). The crude product was diluted with distilled water to make a final volume 5 mL and purified by preparative HPLC system (method B). The radioiodinated product [$^{125}$I]1 trapped in preconditioned Sep Pak C18 cartridge and eluted with methanol (100 μL) to give [$^{125}$I]1 (analytical HPLC retention time 22.5 min, FIG. S9) in high isolated radiochemical yield (95%±3, n=5) and radiochemical purity (>99).

Scheme 1 Synthesis of N-(3,4-dihydroxyphenethyl)-4-iodobenzamide 1, N-(3,4-dihydroxyphenethyl-4-(tributylstannyl)benzamide 2, and [$^{125}$I] 1 compound

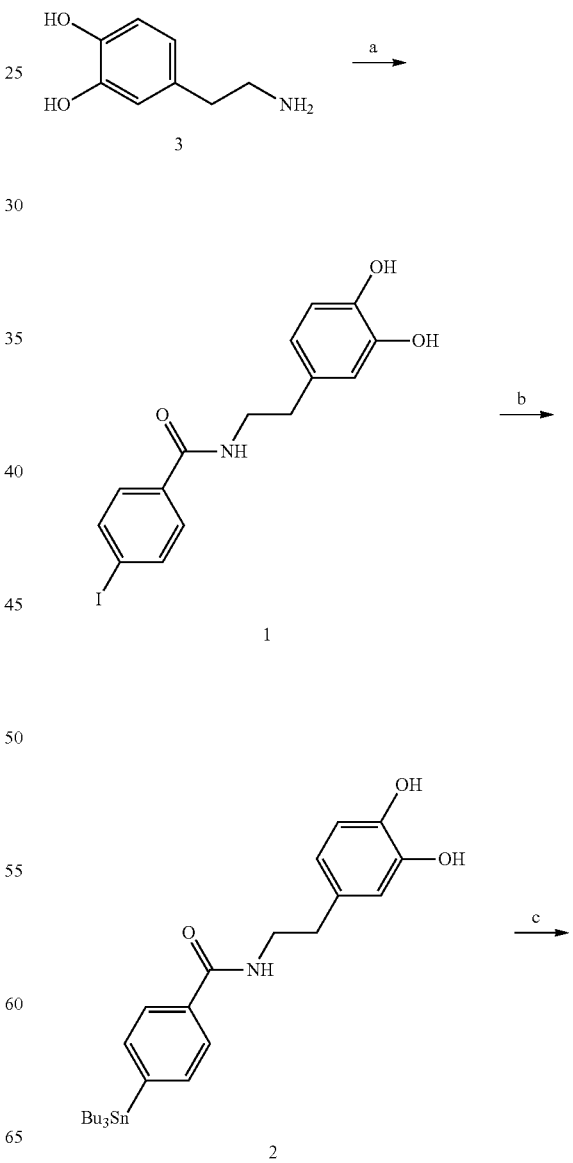

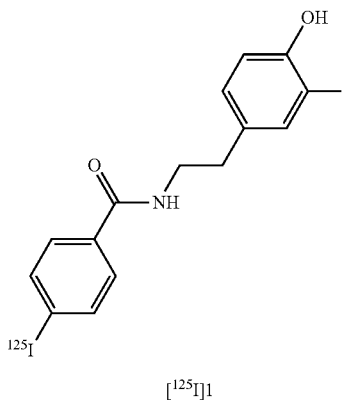

[125I]1

(2) Synthesis of 125I-cRGD Peptide ([125I] 5)

Purified intermediate precursor [125I]1 (200 μCi, 10 μL in methanol) was treated with sodium periodate (NaIO4) (80 μg, 50 μL in water) for 10 min. To this solution intermediate compound 5a (40 μL in methanol) was added. Total reaction volume was 100 μL and final concentration of BCN installed cRGD peptide was 25, 10 or 5 μM. The reaction progress in terms of radiochemical yield was monitored at different points in time using radio-HPLC system (method A) and observed radiolabeling results were summarized in Table 1 below.

Examples 2 and 3: Synthesis of 125I-TF ([125I] 6) and 125I-HSA ([125I]7)

Purified intermediate precursor [125I]1 (200 μCi, 10 μL in methanol) was treated with sodium periodate (NaIO4) (80 μg, 40 μL in water) for 10 min. The reaction mixture was diluted with 40 mL of distilled water and radioactivity was trapped in preconditioned Sep Pak C18 cartridge to remove unreacted NaIO4. Oxidized radiotracer was eluted with 100 μL of methanol and solvent volume was reduced to 10 μL under reduced pressure. The radioactive product was then incubated with 6a or 7a (100 uL, 1×PBS) so that the final concentration of 6a or 7a was 25, 10 or 5 μM. Reaction progress in terms radiolabeling yield was monitored using radio-TLC system at different points in time and important results were summarized in Table 1 below.

TABLE 1

BCN-containing substrates and conditions for reaction with [125I]1

| Entry[a] | BCN installed substrate | Concentration (μmol) | Time (min) | Product | % RCY* |
|---|---|---|---|---|---|
| 1 | c(RGDyK)/5a | 25 | 5 | [125I]5 | 83[b,c] |
| 2 | c(RGDyK)/5a | 25 | 10 | [125I]5 | >99[b,c] |
| 3 | c(RGDyK)/5a | 10 | 10 | [125I]5 | 95[b,c] |
| 4 | THP Protein**/6a | 25 | 15 | [125I]6 | 97[b,d] |
| 5 | THP Protein**/6a | 10 | 15 | [125I]6 | 90[b,d] |
| 6 | THP Protein**/6a | 5 | 15 | [125I]6 | 79[b,d] |
| 7 | HSA Protein***/7a | 25 | 5 | [125I]7 | 77[b,d] |
| 8 | HSA Protein***/7a | 25 | 15 | [125I]7 | >99[b,d] |
| 9 | HSA Protein***/7a | 10 | 15 | [125I]7 | 89[b,d] |

*RCA: Radiochemical yield
**Protein: Transferrin human protein
***HSA Protein: Human serum albumin protein
[a]Solvent system and reaction conditions; entries 1 to 3: methanol/water (1:1), (pH 7.5), rt(room temperature); entries 4 to 9: 10% methanol in 1× PBS solution, (pH 7.5), rt(room temperature).
[b]Reaction with purified [125I]1 after treating with sodium periodate (80 μg).
[c]Radiochemical yield determine by radio-HPLC.
[d]Radiochemical yield determine by radio-TLC.

Scheme 2 Synthesis of [125I] 5 to [125I] 7

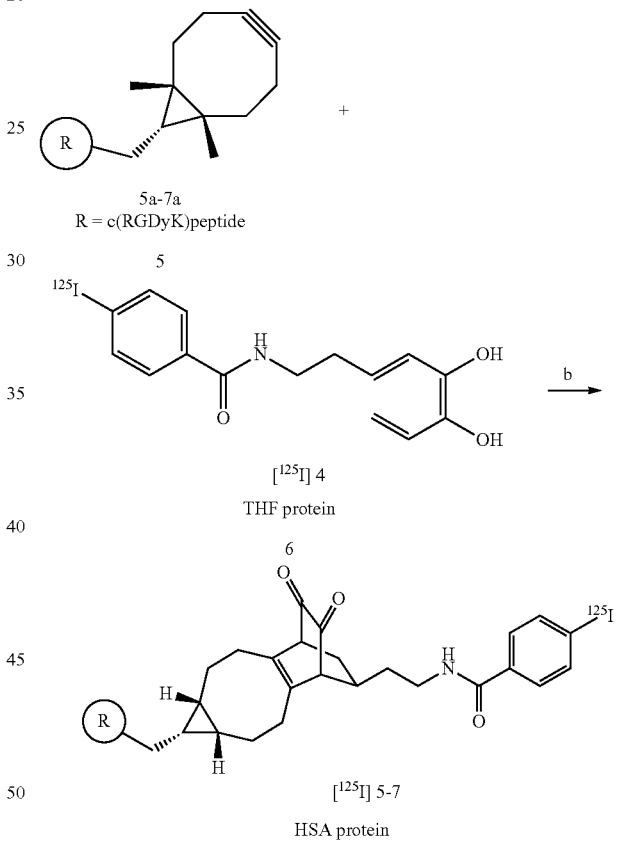

Comparative Example 1: Synthesis of Iodide cRGD Peptide 5b

Intermediate compound 1 (5 mg, 0.013 mmol) dissolved in 1 mL MeOH was treated with sodium periodate (NaIO4) (1 eq, 1 mL H2O) for 10 min. The intermediate compound 5a (10 mg, 0.012 mmol) was added to the reaction mixture. After 30 min crude product was purified by preparative HPLC (method A) to give iodinated cRGD peptide (5b) (12.5 mg, 0.010 mmol, retention time: 19.0 min). MALDI-TOF ([M+H]+) found: 1177.3569.

Scheme 3 Synthesis of iodinated cRGD peptide 5b

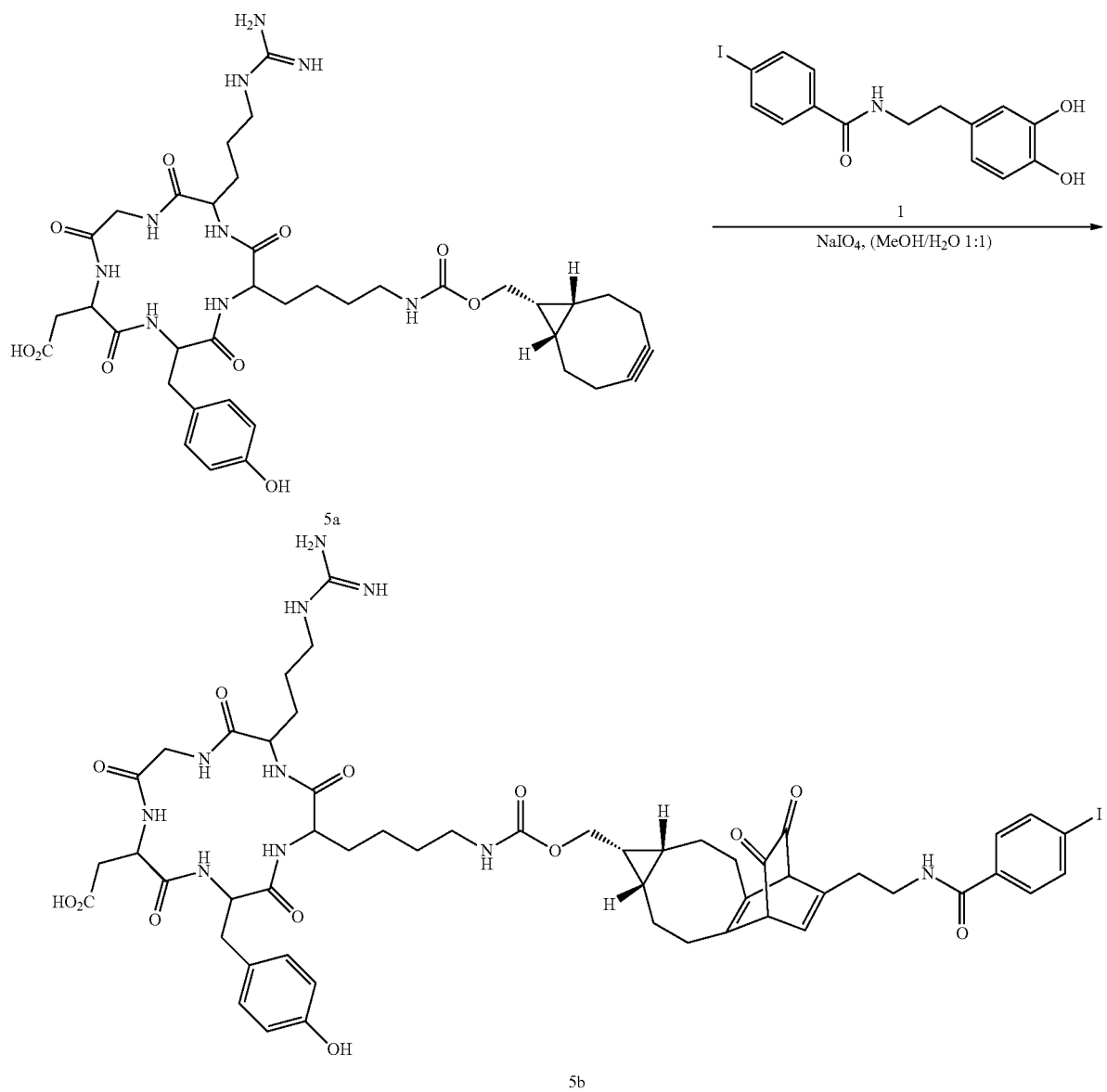

Comparative Example 2: Synthesis of $^{125}$I-HSA (8) (Direct Radioactive Iodide)

HSA (25 μM, 100 μL in saline) was treated with [$^{125}$I]NaI (1 mCi, 3.5 μL) and aqueous solution of chloramine-T (100 μg, 10 μL) for 10 min at 4° C. The reaction was quenched by 10 μL of aqueous sodium metabisulfite solution (1 mg, 20 μl). Crude product was purified by PD-10 desalting column to give [$^{125}$I]8 with 93% radiochemical yield and more than 99% radiochemical purity as determined by radio-TLC system.

Comparative Example 3: Synthesis of $^{125}$I-HSA (9)

Reagent 3-(4-Hydroxyphenyl)propionic acid N-hydroxysuccinimide ester was purchased from Sigma Aldrich, Korea. The radioiodination for HSA protein was performed, according to a procedure published in "Preparation of the iodine-124 derivative of the Bolton-Hunter reagent ([$^{124}$I] I-SHPP) and its use for labelling a VEGF antibody as a PET tracer (Journal of Labelled Compounds and Radiopharmaceuticals. 2002 Oct. 30; 45(12):1077-90, Glaser M". Crude product was purified by PD-10 desalting column to give [$^{125}$I]9 with 85% radiochemical yield and more than 99% radiochemical purity.

5. Biodistribution Study of $^{125}$I-HSA

For detail tissue distribution study 25 ICR male mice were purchased from Orientbio Co., Ltd (Republic of Korea). The animals were randomly divided into 5 groups so that each group contained 5 mice. Each mouse was injected with $^{125}$I-HSA ([$^{125}$I]7), (1 μCi, 100 μL in saline). At given point in time in Table 2, animals were put down and important organs and blood were harvested. Collected organs and blood were weighed and accumulated radioactivity was measured using a gamma counter. The final tissue distribution data were represented as % injected dose per gram of blood or organ of mouse (% ID/g). The results are as shown in FIG. 1.

The tissue distribution of the radioactive iodide HSA proteins 8 and 9 obtained in Comparative Examples 2 and 3, respectively, was also performed in the same procedure. The results were shown in Tables 2 and 3 below.

TABLE 2

Biodistribution results of radioiodinated HSA [$^{125}$I] 8

| | % ID/g $^a$ | | | | | | | | | |
|---|---|---|---|---|---|---|---|---|---|---|
| Time (h) | Blood | Liver | Spleen | Stomach | Small Int. | Large Int. | Kidney | Heart | Lung | Thyroid |
| 0.5 | 31.0 ± 2.02 | 4.98 ± 0.55 | 4.32 ± 1.46 | 1.55 ± 2.02 | 1.77 ± 0.16 | 0.96 ± 0.21 | 7.52 ± 0.96 | 6.35 ± 1.32 | 9.33 ± 1.20 | 3.10 ± 1.11 |
| 1.0 | 30.1 ± 8.47 | 3.10 ± 1.08 | 3.06 ± 1.59 | 2.02 ± 0.99 | 1.78 ± 0.98 | 0.88 ± 0.44 | 5.10 ± 2.22 | 4.55 ± 2.22 | 7.21 ± 2.55 | 4.93 ± 3.20 |
| 4.0 | 12.3 ± 3.04 | 2.72 ± 1.47 | 2.10 ± 0.56 | 10.3 ± 1.08 | 1.66 ± 0.42 | 1.05 ± 0.29 | 3.55 ± 1.25 | 3.67 ± 1.68 | 5.25 ± 1.44 | 59.21 ± 18.50 |
| 16 | 11.2 ± 1.07 | 2.16 ± 0.30 | 1.79 ± 0.47 | 18.4 ± 1.55 | 1.70 ± 0.21 | 1.44 ± 0.26 | 3.10 ± 0.32 | 3.22 ± 1.52 | 6.49 ± 3.21 | 177.65 ± 53.2 |
| 24 | 9.48 ± 1.23 | 1.99 ± 0.33 | 1.67 ± 0.32 | 25.2 ± 4.22 | 1.75 ± 0.40 | 1.47 ± 0.29 | 2.93 ± 0.43 | 2.86 ± 1.10 | 5.21 ± 1.33 | 320.10 ± 78.3 |

$^a$ n = 5 mice per group; % injected dose/gram of organ.

TABLE 3

Biodistribution results of radioiodinated HSA [$^{125}$I]9

| | % ID/g $^a$ | | | | | | | | | |
|---|---|---|---|---|---|---|---|---|---|---|
| Time (h) | Blood | Liver | Spleen | Stomach | Small Int. | Large Int. | Kidney | Heart | Lung | Thyroid |
| 0.5 | 24.0 ± 1.82 | 4.17 ± 0.56 | 3.55 ± 0.66 | 1.61 ± 0.33 | 1.92 ± 0.32 | 0.74 ± 0.12 | 5.88 ± 0.22 | 6.12 ± 1.22 | 7.66 ± 1.22 | 2.44 ± 0.35 |
| 1.0 | 22.9 ± 1.25 | 3.22 ± 0.49 | 3.21 ± 0.81 | 2.00 ± 0.90 | 2.65 ± 0.26 | 1.31 ± 0.17 | 6.22 ± 0.57 | 5.44 ± 0.77 | 6.66 ± 0.87 | 3.38 ± 1.61 |
| 4.0 | 15.81 ± 0.95 | 3.53 ± 0.62 | 2.88 ± 0.44 | 8.21 ± 3.11 | 2.75 ± 0.32 | 2.01 ± 0.27 | 6.31 ± 0.76 | 4.28 ± 0.86 | 6.25 ± 2.31 | 50.21 ± 9.30 |
| 16 | 7.41 ± 0.78 | 2.42 ± 0.28 | 1.58 ± 0.20 | 10.3 ± 2.41 | 2.85 ± 0.30 | 2.74 ± 0.23 | 3.88 ± 0.33 | 2.32 ± 0.47 | 4.22 ± 0.47 | 130.65 ± 45.3 |
| 24 | 5.51 ± 0.48 | 1.85 ± 0.45 | 1.16 ± 0.17 | 19.1 ± 3.95 | 2.80 ± 0.29 | 1.99 ± 0.10 | 4.84 ± 0.18 | 2.01 ± 1.11 | 3.85 ± 2.32 | 298.10 ± 95.0 |

$^a$ n = 5 mice per group; % injected dose/gram of organ.

6. Competitive Reaction Study

To determine the reaction preference of oxidized [$^{125}$I]1 toward BCN group two sets of experiments were conducted.

In experiment (I), oxidized [$^{125}$I]1 (200 µCi, 20 µL in methanol) was incubated with a mixture containing BCN installed cRGD peptide (25 µM) and non modified HSA protein (25 µM) in 200 µL of 1×PBS at rt (pH 7.5). The reaction was carried out for 30 min and subjected to centrifugation (4500 rpm, 12 min, 4° C.) using 50 kDa Amicon filter. The radioactivity associated to cRGD peptide (filtrate) or HSA protein (residue) was determine using gamma counter system.

In experiment (II), oxidized [$^{125}$I]1 (200 µCi, 20 µL in methanol) was incubated with BCN installed HSA protein (25 µM) and non modified cRGD peptide (25 µM) under similar conditions used for experiments (I).

Each experiment was repeated 3 times and products identity was confirmed by radio-HPLC or radio-TLC system. The final radiolabeling results were summarized in Table 4 below.

TABLE 4

Radiolabeling results for competitive reaction studies

| Experiment | Molecule | % RCY | $^{125}$I-molecule |
|---|---|---|---|
| II | c(RGDyK) 25 µmol + HSA-BCN 25 µmol | 93-97 | $^{125}$I-HSA |

TABLE 4-continued

Radiolabeling results for competitive reaction studies

| Experiment | Molecule | % RCY | $^{125}$I-molecule |
|---|---|---|---|
| I | c(RGDyK)-BCN 25 µmol + HSA 25 µmol | 90-94 | $^{125}$I-c(RGDyK) |

* RCY: Radiochemical yield

Figure 2:
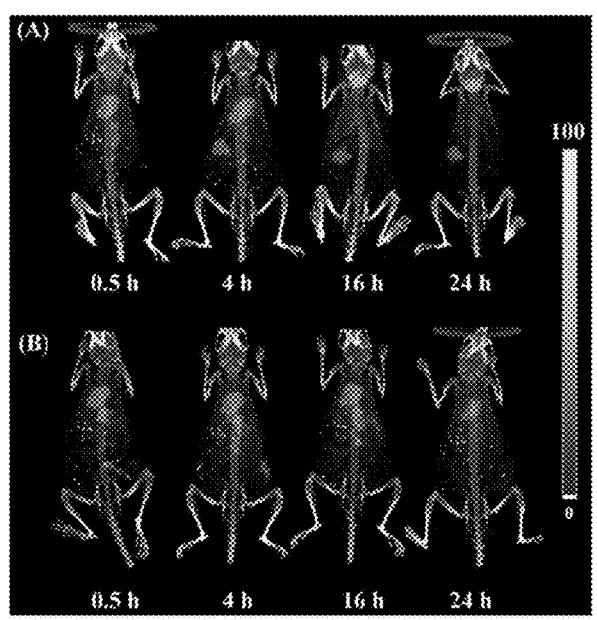
FIG. 2 shows SPECT/CT images of radioiodized HSA at various points in time after intravenous injection in normal mice, in which portion (B) shows the results of 150 μCi of purified radioiodinated HSA, synthesized using ([$^{125}$I] 7) of Inventive Example 3 according to the present disclosure, and portion (A) shows the results of 150 μCi of purified radioiodinated HSA, synthesized using the direct radioiodination ([$^{125}$I] 8) of Comparative Example 2.
Figure 3:
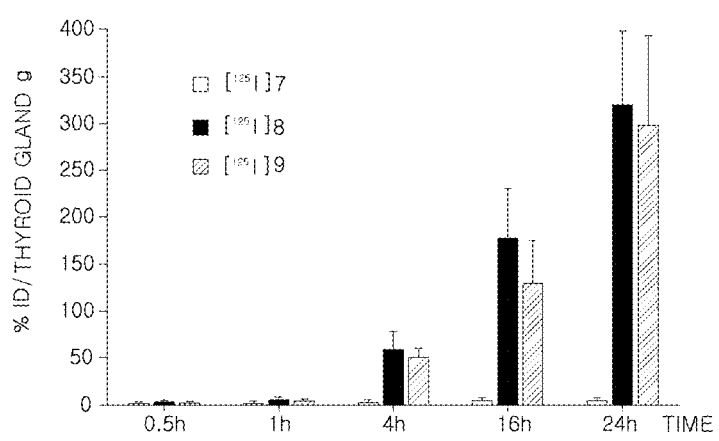
FIG. 3 shows uptake of free $^{125}$I in the thyroid gland from radioiodinated HSA [$^{125}$I] 7, [$^{125}$I] 8, and [$^{125}$I] 9.

7. SPECT/CT Imaging of $^{125}$I-HSA $^{125}$I-HSA ([$^{125}$I]7) (150 µCi, 100 µL in saline), was intravenously injected to ICR mouse. At given point in time (0.25, 1, 4, 16, 24 h) SPECT/CT images were acquired. The results are shown in portion (B) of FIG. 2.

For comparison, SPECT/CT images were also acquired for [$^{125}$I]8 using same procedure. The results were shown in portion (A) of FIG. 2.

8. Comparison of Thyroid Uptake of Free Radioiodine from [$^{125}$I]7 [$^{125}$I]8 or [$^{125}$I] 9

In vivo deiodination and uptake of free $^{125}$I in thyroid from radioiodinated HSA [$^{125}$I]7, [$^{125}$I]8 or [$^{125}$I]9. The radioiodinated HSA [$^{125}$I]7 (SPOCQ based radioiodination) found to be more stable as compared with other two radioiodination strategies.

According to an embodiment of the present disclosure, in a case of labeling a radioisotope using a quinone compound labeled with a radioisotope, since this has a higher stability in vivo than those of the conventional technologies, accumulation of iodine-125 in a thyroid gland may be significantly reduced, a reaction rate with a cyclooctyne compound to which a biomolecule, a fluorescent dye, or a nanoparticle compound is bound may be relatively fast, and stability in vivo may be relatively high, to be usefully applied to medical diagnostic and therapeutic compositions.

While example embodiments have been shown and described above, it will be apparent to those skilled in the art that modifications and variations could be made without departing from the scope of the present disclosure as defined by the appended claims.

What is claimed is:

1. A method of producing a labeled biomolecule, fluorescent dye, or nanoparticle compound wherein the labeled biomolecule, fluorescent dye, or nanoparticle compound has a structure of Formula (III),

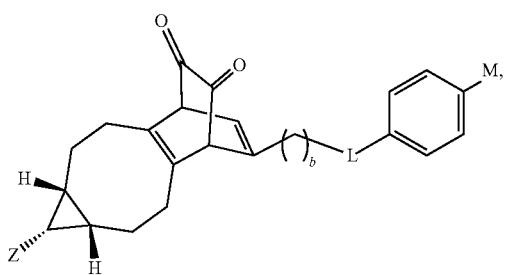

the method comprising:
reacting a cyclooctyne compound having a structure of formula (I),

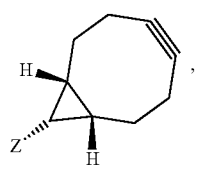

with a quinone compound having a structure of formula (II):

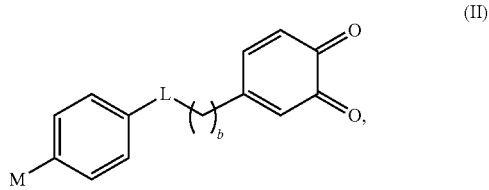

wherein:
Z is selected from the group consisting of a biomolecule, a fluorescent dye, or a nanoparticle; b is 0 or an integer from 1 to 10; L is $CH_2$, —COO—, or —CONH—; and M is a radioisotope.

2. The method according to claim 1, wherein the reacting is performed at room temperature and atmospheric conditions.

3. The method according to claim 1, wherein the reacting is performed in an aqueous solution.

4. The method according to claim 1, wherein the biomolecule is at least one selected from the group consisting of a peptide, an affibody, an antibody, and an oligonucleotide.

5. The method according to claim 1, wherein the nanoparticle compound is at least one selected from the group consisting of a metal nanoparticle, a synthetic polymer nanoparticle, and a biopolymer nanoparticle.

6. The method according to claim 5, wherein the metal nanoparticle is any one metal selected from the group consisting of gold (Au), platinum (Pt), palladium (Pd), silver (Ag), and copper (Cu), or an oxide of any one metal selected from the group consisting of cobalt (Co), manganese (Mn), iron (Fe), nickel (Ni), gadolinium (Gd), molybdenum (Mo), zinc (Zn), and chromium (Cr).

7. The method according to claim 1, wherein the fluorescent dye is at least one selected from a cyanine dye, a fluorescein dye, and a rhodamine dye.

8. The method according to claim 1, wherein the radioisotope M is selected from the group consisting of I, F, Tc, Re, Ga, In, Zr, Y, Ho, Sm, and Lu.

9. The method according to claim 1, wherein the radioisotope M is at least one radioactive iodine selected from the group consisting of $^{122}$I, $^{123}$I, $^{124}$I, $^{125}$I, $^{127}$I, $^{131}$I, and $^{132}$I.

* * * * *